United States Patent
Fiveland et al.

(10) Patent No.: US 10,624,588 B2
(45) Date of Patent: *Apr. 21, 2020

(54) SYSTEM AND METHOD FOR PREDICTING AN EXCITATION PATTERN OF A DEEP BRAIN STIMULATION

(71) Applicant: General Electric Company, Schenectady, NY (US)

(72) Inventors: Eric William Fiveland, Niskayuna, NY (US); Ileana Hancu, Clifton Park, NY (US); Jeffrey Ashe, Gloversville, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 487 days.

This patent is subject to a terminal disclaimer.

(21) Appl. No.: 15/406,895

(22) Filed: Jan. 16, 2017

(65) Prior Publication Data

US 2018/0199895 A1   Jul. 19, 2018

(51) Int. Cl.
*A61B 5/0476* (2006.01)
*A61B 5/00* (2006.01)
(Continued)

(52) U.S. Cl.
CPC .......... *A61B 5/7285* (2013.01); *A61B 5/0042* (2013.01); *A61B 5/04004* (2013.01);
(Continued)

(58) Field of Classification Search
CPC .. A61B 5/7285; A61B 5/7292; G01R 33/567; G01R 33/5673; G01R 33/5676
See application file for complete search history.

(56) References Cited

U.S. PATENT DOCUMENTS 6,066,163 A   5/2000   John
6,198,958 B1  3/2001   Ives et al.
(Continued)

FOREIGN PATENT DOCUMENTS

WO   2006102370 A2   9/2006
WO   2011133583 A1   10/2011
(Continued)

OTHER PUBLICATIONS

International Search Report and Written Opinion issued in connection with PCT Application No. PCT/US2018/013499 dated Apr. 27, 2018.

(Continued)

*Primary Examiner* — George R Evanisko
(74) *Attorney, Agent, or Firm* — Fletcher Yoder, P.C.

(57) ABSTRACT

A system and method for analyzing bioelectrical signals generated during a deep brain stimulation (DBS) includes an apparatus having a housing having a signal input and a signal output and an electrical circuit disposed within the housing and electrically coupled between the signal input and the signal output. The electrical circuit is configured to receive bioelectrical signals corresponding to a cyclic excitation signal transmitted by a pulse generator during a DBS and generate an output signal comprising a series of timing pulses, wherein each timing pulse simulates an envelope of the cyclic excitation signal. The signal output of the housing is electrically coupleable to an auxiliary trigger input of an imaging system and the series of timing pulses can be used to trigger image data acquisition.

20 Claims, 5 Drawing Sheets

(51) Int. Cl.

| | | |
|---|---|---|
| *A61B 5/04* | (2006.01) | |
| *A61B 5/0408* | (2006.01) | |
| *A61B 5/055* | (2006.01) | |
| *A61N 1/36* | (2006.01) | |
| *A61B 6/03* | (2006.01) | |
| *G01R 33/48* | (2006.01) | |
| *A61B 5/0482* | (2006.01) | |
| *A61B 5/0478* | (2006.01) | |
| *A61N 1/05* | (2006.01) | |

(52) U.S. Cl.
CPC ........ *A61B 5/0408* (2013.01); *A61B 5/04017* (2013.01); *A61B 5/0476* (2013.01); *A61B 5/055* (2013.01); *A61B 5/7435* (2013.01); *A61N 1/3605* (2013.01); *A61B 5/0478* (2013.01); *A61B 5/0482* (2013.01); *A61B 5/7203* (2013.01); *A61B 5/7257* (2013.01); *A61B 6/037* (2013.01); *A61N 1/0534* (2013.01); *A61N 1/3606* (2013.01); *G01R 33/4806* (2013.01)

(56) References Cited

U.S. PATENT DOCUMENTS

| | | | |
|---|---|---|---|
| 6,463,328 | B1 | 10/2002 | John |
| 7,706,871 | B2 | 4/2010 | Devlin et al. |
| 8,214,055 | B2 | 7/2012 | Erickson |
| 8,280,514 | B2 | 10/2012 | Lozano et al. |
| 8,295,935 | B2 | 10/2012 | Okun et al. |
| 8,315,703 | B2 | 11/2012 | Lozano |
| 9,050,469 | B1 | 6/2015 | Osorio et al. |
| 2005/0228461 | A1 | 10/2005 | Osorio et al. |
| 2005/0240242 | A1 | 10/2005 | DiLorenzo |
| 2007/0142874 | A1 | 6/2007 | John |
| 2008/0039709 | A1 | 2/2008 | Karmarkar |
| 2008/0208258 | A1 | 8/2008 | Foley et al. |
| 2008/0208285 | A1 | 8/2008 | Fowler et al. |
| 2009/0062676 | A1* | 3/2009 | Kruglikov ............ A61B 5/0484 600/544 |
| 2009/0171184 | A1 | 7/2009 | Jenkins et al. |
| 2011/0112394 | A1 | 5/2011 | Mishelevich |
| 2011/0130615 | A1 | 6/2011 | Mishelevich |
| 2012/0220812 | A1 | 8/2012 | Mishelevich |
| 2012/0226091 | A1 | 9/2012 | Mishelevich |
| 2012/0232433 | A1 | 9/2012 | Mishelevich |
| 2012/0245493 | A1 | 9/2012 | Mishelevich |
| 2012/0277820 | A1 | 11/2012 | Wu et al. |
| 2012/0283502 | A1 | 11/2012 | Mishelevich et al. |
| 2012/0296241 | A1 | 11/2012 | Mishelevich |
| 2012/0316427 | A1 | 12/2012 | Zeijlemaker et al. |
| 2013/0066350 | A1 | 3/2013 | Mishelevich |
| 2013/0144192 | A1 | 6/2013 | Mishelevich et al. |
| 2013/0261506 | A1 | 10/2013 | Mishelevich |
| 2014/0094719 | A1 | 4/2014 | Mishelevich |
| 2014/0194726 | A1 | 7/2014 | Mishelevich et al. |
| 2015/0360039 | A1 | 12/2015 | Lempka et al. |
| 2015/0366482 | A1 | 12/2015 | Lee |
| 2016/0220836 | A1 | 8/2016 | Parks |
| 2018/0199892 | A1 | 7/2018 | Fiveland et al. |

FOREIGN PATENT DOCUMENTS

| | | |
|---|---|---|
| WO | 2012164172 A1 | 12/2012 |
| WO | 2014/047179 A1 | 3/2014 |

OTHER PUBLICATIONS

Fontaine et al., "Symptomatic Treatment of Memory Decline in Alzheimer's Disease by Deep Brain Stimulation: A Feasibility Study", Journal of Alzheimer's Disease, vol. 34, Issue 01, 2013, pp. 315-323.

Lavano et al., "Deep Brain Stimulation for Alzheimer's Disease", Brain Disorders & Therapy, vol. 6, Issue 1, 2016, pp. 1-4.

Jech et al., Functional Magnetic Resonance Imaging During Deep Brain Stimulation: A Pilot Study in Four Patients with Parkinson's Disease, ResearchGate, Movement Disorders, vol. 16, No. 4, 2001, pp. 1126-1132.

Knight et al., "Motor and Non-Motor Circuitry Activation Induced by Subthalamic Nucleus Deep Brain Stimulation (STN DBS) in Parkinson's Disease Patients: Intraoperative fMRI for DBS", Mayo Clin Proc., vol. 90, No. 6, Jun. 2015, pp. 773-785.

Phillips et al., "Parkinson Disease: Pattern of Functional MR Imaging Activation during Deep Brain Stimulation of Subthalamic Nucleus—Initial Experience", Radiology, RSNA, vol. 239, No. 1, Apr. 2006, pp. 209-216.

International Search Report and Written Opinion issued in connection with corresponding PCT Application No. PCT/US2018/013498 dated Apr. 30, 2018.

* cited by examiner

SYSTEM AND METHOD FOR PREDICTING AN EXCITATION PATTERN OF A DEEP BRAIN STIMULATION

BACKGROUND OF THE INVENTION

Embodiments of the invention relate generally to a system and method for synchronizing image data acquisition with a deep brain stimulation, and more particularly to a system and method that generates a timing pulse for triggering image data acquisition from bioelectrical data acquired during short term cycling of a deep brain stimulation.

Deep brain stimulation (DBS) is used for treating disabling neurological symptoms and psychiatric disorders. The procedure uses a neurostimulator to deliver electrical stimulation to the brain by way of surgically implanted electrodes. Depending on the condition being treated, the electrodes can be used to target certain cells and chemicals within the brain or can be targeted toward areas of the brain that control movement or regulate abnormal impulses. In this later case, the electrical stimulation can be used to disrupt abnormal nerve signals that cause tremor and other neurological symptoms. Over the past 20 years, more than 100,000 Parkinson's disease, essential tremor, dystonia and obsessive-compulsive disorder patients have seen significant symptom relief due to DBS treatment. Evidence now accumulates indicating that patients with chronic pain, post-traumatic stress disorder, and obesity may also benefit from DBS treatments.

Despite the long history of DBS, its underlying principles and mechanisms are still not clear. In particular, the understanding of how the brain responds to different DBS excitation parameters, such as electrode choice, frequency, current/voltage and pulsewidth is limited. There is no real time feedback mechanism to let a clinician decide whether DBS has its intended effect or whether the stimulation parameters are optimal for each individual patient. The only current option is to watch the patient evolve over a signification period of time, often months, and determine thereafter if symptoms improve. Feedback in the form of qualitative or quantitative measurements of brain response to DBS may aid in optimizing the DBS excitation parameters for treating conditions such as dystonia or depression.

Functional magnetic resonance imaging (fMRI) is one of the few non-invasive tools that could be used for such feedback. In particular, fMRI might be used to provide a quick and efficient feedback mechanism by highlighting areas of brain activity related to DBS stimulation and allowing optimization of DBS stimulation parameters in close to real time. However, fMRI is currently not easily achievable in patients with implanted DBS pulse generators due to the longstanding FDA restriction that prohibits patients with implanted DBS pulse generators from undergoing MRI Recent label changes for Medtronic® DBS hardware permit patients with internalized pulse generator hardware to undergo MRI during active DBS. While DBS electrodes can be cycled ON and OFF during a given DBS, there is no way to know whether the DBS excitation cycle is in the ON or OFF condition when the patient is inside the MRI scanner because the programming of the DBS device can only be done outside the MRI scanner. Even if the parameters of the DBS were known prior to fMRI acquisition, a multi-second time lag occurs during which the stimulation parameters are communicated from the controller to the pulse generator and thereafter from the pulse generator to the electrodes resulting in differences between the requested and measured stimulation periods. This communication time lag and the long time interval between the pulse generator programming and actual fMRI onset can lead to large errors in assessing the stimulation state, which can cause significant drops in fMRI sensitivity. Consequently, fMRI imaging data cannot be properly binned corresponding to ON and OFF conditions of the DBS excitation cycle.

It would therefore be desirable to have a system and method capable of accurately detecting the timing of the excitation pattern of a DBS and predicting a future timing pattern of the excitation pattern. It would also be desirable for such a system and method to generate an output from the future timing pattern in the form of a time stamp log to permit medical images acquired during DBS excitation to be binned in a manner corresponding to the DBS excitation. It would also be desirable for such a system and method to enable medical data acquisition to be synchronized with the ON and OFF conditions of a DBS excitation cycle such that brain regions activated as a consequence of the DBS may be identified in the acquired medical data. It would further be desirable to produce an output representative of the DBS excitation pattern to facilitate analysis of the health of the DBS system.

BRIEF DESCRIPTION OF THE INVENTION

In accordance with one aspect of the invention, an apparatus for analyzing bioelectrical signals generated during a deep brain stimulation (DBS) includes a housing having a signal input and a signal output and an electrical circuit disposed within the housing and electrically coupled between the signal input and the signal output. The electrical circuit is configured to receive bioelectrical signals corresponding to a cyclic excitation signal transmitted by a pulse generator during a DBS and generate an output signal comprising a series of timing pulses, wherein each timing pulse simulates an envelope of the cyclic excitation signal.

In accordance with another aspect of the invention, a method for analyzing bioelectrical signals generated during a deep brain stimulation (DBS) includes obtaining bioelectrical signals generated from excitation signals transmitted by a pulse generator during a DBS. The method also includes transforming the bioelectrical signals into a series of digital logic pulses representing a plurality of active portions of the DBS, each active portion comprising a plurality of digital logic pulses. The method further includes generating a series of timing pulses from the series of digital logic pulses, each timing pulse synchronized with predicted timing of an active portion of the DBS.

In accordance with yet another aspect of the invention, a medical imaging system includes an imaging device configured to acquire medical image data from a patient and reconstruct medical images therefrom. The medical imaging system also includes a sensor system configured to detect bioelectrical signals generated within the patient during a deep brain stimulation (DBS) and a DBS signal emulator removeably coupleable to a trigger input of the imaging device and to the sensor system. The DBS signal emulator is programmed to transform bioelectrical signals received from the sensor system into a series of timing pulses having pulse widths predictive of active periods of the DBS and output the series of timing pulses to the trigger input of the imaging device.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

In general, embodiments of the invention described herein are directed to a system and method for detecting the excitation pattern of a deep brain stimulation (DBS) and converting the detected excitation pattern into a timing pulse that permits image data acquisition to be synchronized with the DBS.

While embodiments of the invention are discussed below in regard to synchronizing DBS with the acquisition of functional magnetic resonance image (fMRI) data, the systems and methods disclosed herein may be used with alternative image data acquisition techniques, including positron emission tomography (PET) and optical imaging. The techniques described herein may also be used in conjunction with electroencephalography (EEG) or magnetoencephalography (MEG) to pick up the functional response of a DBS system with the associated detectors. Still further, the techniques described herein may be utilized to analyze the health of a DBS system and determine whether the DBS system is transmitting stimulation signals in accordance with desired program parameters.

Figure 1:
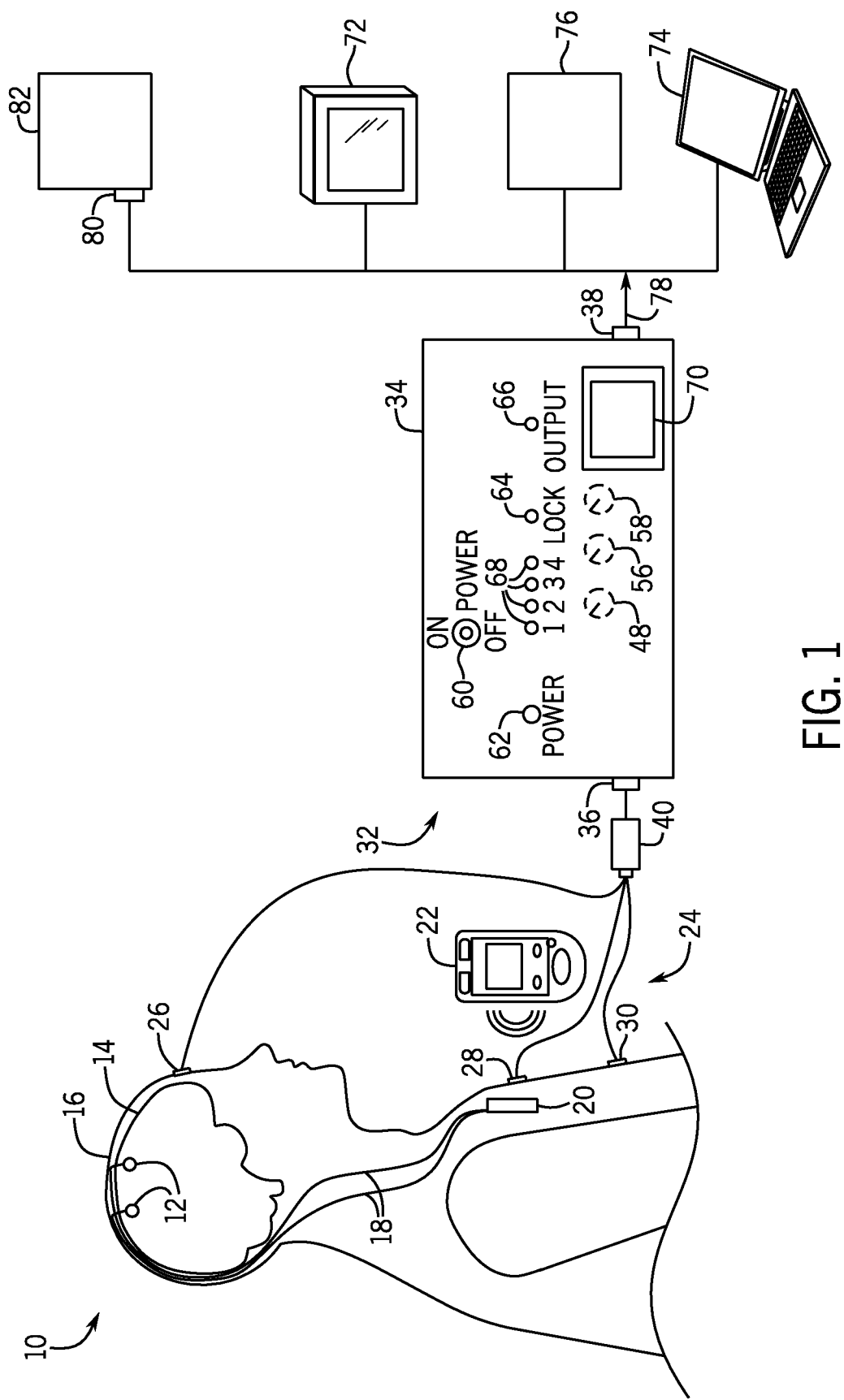
FIG. 1 is a schematic block diagram of a deep brain stimulation (DBS) detection system, according to an embodiment of the invention.

FIG. 1 depicts a deep brain stimulation (DBS) detection system 10 according to one embodiment of the invention. The DBS detection system 10 includes one or more leads or electrodes 12 surgically implanted within the one or more regions of the brain 14 of a patient 16. Each implanted electrode 12 is configured to apply stimulation signals to a targeted region of the brain 14. While two electrodes 12 are illustrated in FIG. 1, it will be understood that system 10 may include a single implanted electrode as well as three or more electrodes, each of which may be positioned and configured to facilitate unipolar or bipolar stimulation.

Each implanted electrode 12 is connected through an extension wire 18 that is passed under the skin of the patient 16 to a pulse generator 20 configured to deliver stimulation signals to electrodes 12. Pulse generator 20 may include a power supply (not shown) such as a battery or other type of power storage device and microelectronic circuitry (not shown) that may include hardware and/or software for generating and outputting stimulation signals in response to control signals or commands. In some embodiments, pulse generator 20 may further include a storage unit (not shown) that permits patient-specific data to be stored within the pulse generator 20.

In the illustrated embodiment, pulse generator 20 is an internal pulse generator that is implanted beneath the skin of the patient 16, such as, for example, under the clavicle as shown in FIG. 1. However, internal pulse generator 20 may be located elsewhere within the patient 16 in alternative embodiments such as, for example, lower in the chest or over the abdomen. As one non-limiting example, internal pulse generator 20 is an Activa PC Neurostimulator manufactured by Medtronic®. In alternative embodiments, pulse generator 20 may be an external device coupled to implanted electrodes 12.

In the case of an implanted pulse generator, the pulse generator 20 is programmed with a wireless device 22 that is held over the skin of the patient 16 proximate the implanted location of the pulse generator 20. The programming defines the excitation parameters of the DBS, which can be adjusted as the patient's condition changes over time. The circuitry within the pulse generator 20 generates pulse sequences in accordance with the stimulation parameters that send excitation signals to implanted electrodes 12. The stimulation can be provided in a cycling fashion and at various currents, voltages, frequencies, and pulse widths based on the desired treatment.

A sensor system 24 is provided to sense and track the stimulation signal transmitted by the internal pulse generator 20 to the implanted electrodes 12. In one embodiment, sensor system 24 is an arrangement of three EKG electrodes 26, 28, 30 that are affixed to the skin surface of the patient 16 to measure bioelectrical signals from the patient 16, which include physiological signals generated by the patient's anatomy (e.g., the heart) and voltages generated by the small currents flowing through the patient 16 as a consequence of the DBS. In the illustrated embodiment, EKG electrodes 26, 28, 30 are applied to the patient 16 proximate the forehead, near the internal pulse generator 20, and abdomen respectively and may be used to sense a DBS excitation pattern generated by implanted electrodes 12 configured for bipolar and/or monopolar operation modes. However, a skilled artisan will recognize that EKG electrodes 26, 28, 30 may be positioned in alternative locations on the patient 16 such as on the multiple locations on the chest or left arm, right arm, and at a reference location, as non-limiting examples, in embodiments that utilize electrodes 12 configured for monopolar operation. In yet alternative embodiments, sensor system 24 may include sensors provided in the form of loops or plates (not shown) that are configured to pick up the DBS signals through inductive or capacitive coupling to the internal pulse generator 20.

A DBS waveform emulator 32 is used in conjunction with the sensor system 24 to detect the DBS excitation pattern generated by the internal pulse generator 20 and transform the detected signal into a pulse sequence that emulates the detected pattern. DBS waveform emulator 32 includes a housing 34 with at least one input port 36 and at least one output port 38. A bio-amplifier 40, such as a commercial device, ETH-256, manufactured by iWorx, Dover, N.H. as a non-limiting example, is coupled between sensor system 24 and the input port 36 of DBS waveform emulator 32 to electrically isolate the patient 16 from the DBS waveform emulator 32 and amplify the incoming signal from EKG electrodes 26, 28, 30. In an alternative, embodiment bio-amplifier 40 may be integrated within the housing 34 of DBS waveform emulator 32.

Figure 2:
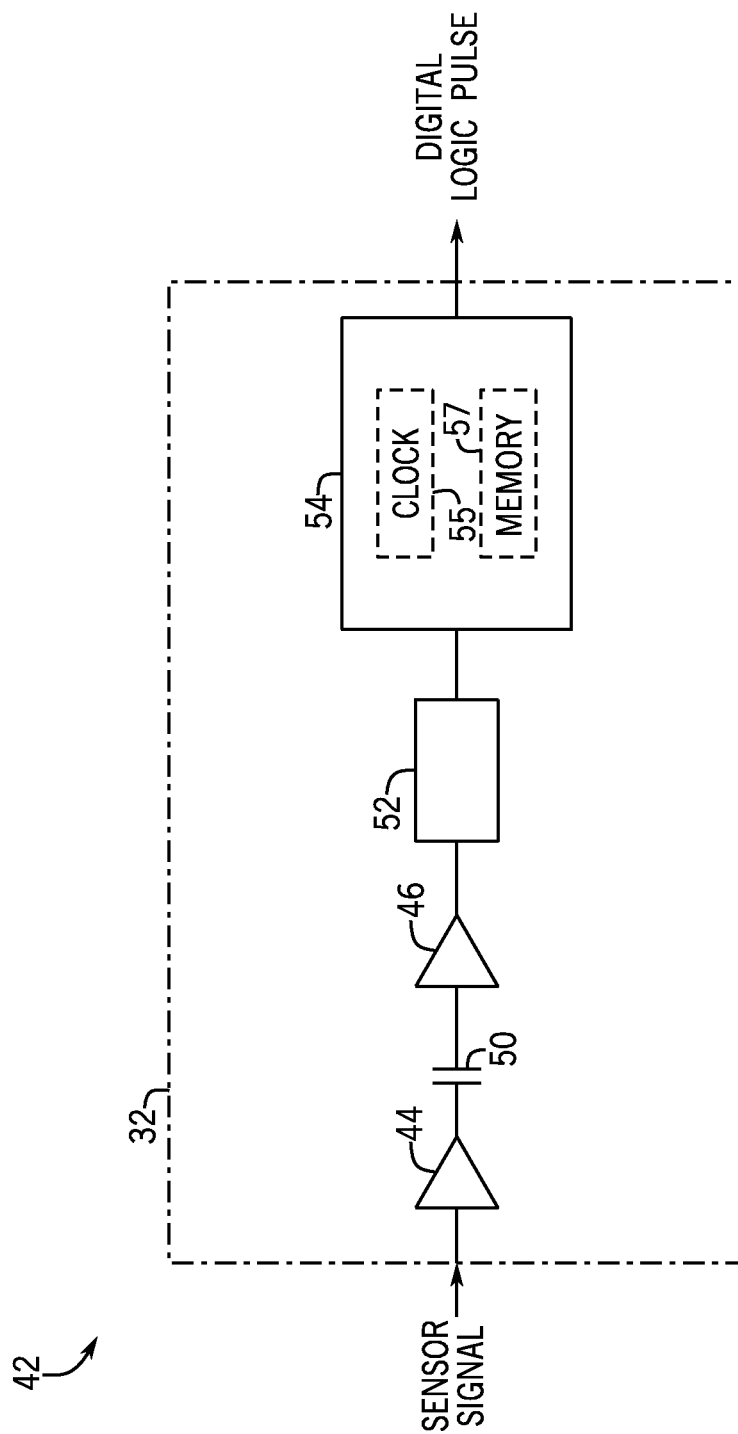
FIG. 2 is a schematic diagram of an electrical circuit employed in a DBS waveform emulator integrated within the DBS detection system of FIG. 1, according to an embodiment of the invention.

An electrical circuit 42, illustrated in FIG. 2, is provided within the housing 34 of DBS waveform emulator 32 and coupled between the input port 36 and output port 38 thereof. As described in more detail below, the electrical circuit 42 is configured to transform bioelectrical signals received from sensor system 24 into a series of pulses that represent predicted active periods and non-active periods of a cyclic deep brain stimulation. The electrical circuit 42 includes one or more filters 44 that eliminate artifacts caused by non-brain sources from the incoming, raw signal received from bio-amplifier 40. In one non-limiting embodiment, filter 44 is a 100 Hz high pass filter configured to remove the heart signal. However, it is contemplated that high pass filter 44 may be alternatively configured to remove other undesirable frequency components from the raw signal.

DBS waveform emulator 32 also includes a logic buffer or comparator circuit 46 that performs an analog-to-digital signal conversion with an adjustable threshold and separates the actual DBS signal generated by internal pulse generator 20 from noise. This adjustable threshold may be manually adjusted using an adjustment dial 48 (FIG. 1) provided on the DBS waveform emulator 32 or, in alternative embodiments, using an algorithm that sets the threshold. In one embodiment comparator circuit 46 performs a transistor-transistor logic (TTL) signal conversion. Alternatively, comparator circuit 46 may be configured to output other digital logic signals, including CMOS, ICL, or LVDS as non-limiting examples. A DC-blocking capacitor 50 may be provided between the high pass filter 44 and comparator circuit 46. Alternatively, the DC-blocking functionality may be integrated within the high pass filter 44. A pulse stretcher 52 coupled to the output of the comparator circuit 46 ensures that a single TTL signal is generated for a single incoming DBS pulse. The resulting output from pulse stretcher 52 is a series of digital logic pulses that represent active portions of the cyclic DBS excitation pattern, with each active portion of the pattern including a series of individual digital logic pulses representative of the multiple excitation signals delivered during a respective ON portion of an ON/OFF cycle of the DBS excitation.

A microprocessor 54 receives the series of digital logic pulses from the pulse stretcher 52. In one embodiment microprocessor 54 is an Arduino Micro microprocessor. However, one skilled in the art will recognize that any suitable microprocessor may be used to carry out the desired operations, which include detecting the start and stop times of the pulse cycles and ignoring noise and erroneous signals in the filtered data. The microprocessor 54 is programmed to record the pulse timing of the cyclic DBS excitation pattern in real time and calculate the period of the cyclic excitation pattern by averaging multiple cycles. After recording the pulse timing, microprocessor 54 generates an output that emulates the DBS waveform. In one embodiment, the output is in the form of a log of time stamps that predict the start time and duration of future active transmission periods of neurological excitation. In such an embodiment the microprocessor 54 may be configured to optionally include a clock (55) 55 (shown in phantom) that records timing of the digital logic pulses and is used as a reference for the generated time stamp log. Microprocessor 54 may further be configured having an optional memory 57 (shown in phantom) for storing the generated time stamp log. Alternatively, the time stamp log may output to an auxiliary storage device, such as, for example, computer 74 or database 76 of FIG. 1.

In another embodiment, the output generated by the microprocessor 54 is in the form of a series of timing pulses. The timing pulses of the output signal simulate the envelope of the cyclic DBS excitation pattern, with the pulse width of each timing pulse approximating the duration of an active or ON portion of a respective ON/OFF cycle. The microprocessor 54 is further programmed to identify a signal lock if the number of recorded digital logic pulses exceeds a predetermined threshold, as described in more detail below.

Referring again to FIG. 1, in some embodiments DBS waveform emulator 32 further includes one or more additional inputs or dials 56, 58 (shown in phantom) that permit an operator to input one or more expected parameters of the DBS stimulation to the microprocessor 54. In one embodiment, dial 56 is used to indicate the total expected, programmed period of the DBS—that is the sum of the ON and OFF portions of a signal period. Dial 58 represents the expected frequency programmed in pulse generator 20.

A power switch 60 is provided on the housing 34 for controlling the supply of power to DBS waveform emulator 32. An optional power indicating light 62 (shown in phantom) may be provided on the housing 34 to identify the ON/OFF status of DBS waveform emulator 32. DBS waveform emulator 32 may further include an operator indicator 64 that signals when DBS waveform emulator 32 is locked on the stimulation signal generated by pulse generator 20. In the illustrated embodiment, the operator indicator 64 is provided in the form of a lock light. However, it is contemplated that DBS waveform emulator 32 may be configured to include a speaker (not shown) that outputs an audible signal upon acquiring a signal lock. This speaker may further be configured to generate an audible signal representative of the digital logic signal from the pulse stretcher 52, which may be used by the operator in threshold adjustments. An output light 66 is also provided on housing 34 that indicates when DBS waveform emulator 32 is outputting a TTL signal predictive of the DBS. One or more additional indicator lights 68 (shown in phantom) may optionally be included on housing 34 to indicate the status of intermediate processing steps being carried out by the electrical circuit 42.

DBS waveform emulator 32 further includes a display 70, such as an LCD display for example, that may be configured to report various parameters relevant to the signal transformation. As non-limiting examples, display 70 may include the frequency as the adjustment dial 48 is manipulated, timing of the measured ON and OFF periods of the DBS stimulation, a measured difference or wander between the actual (measured) timing of the ON and OFF periods and the predicted timing of the ON and OFF periods after signal lock, and/or an elapsed time from signal lock.

Data measured in real time, including the time stamps of the measured and predicted pulses can be output from the DBS waveform emulator 32 for display on an auxiliary display 72 and/or output to a serial port connection, which can be read by a computer 74 or other device. The output port 38 of DBS waveform emulator 32 may be also be connected to a database 76 for storage and later retrieval of data corresponding to the detected DBS excitation pattern received from sensor system 24 and the digital logic pulse or output timing signal 78 generated by microprocessor 54. In another embodiment described in additional below, the output port 38 of DBS waveform emulator 32 is coupled to an auxiliary trigger input or input data acquisition board 80 of an imaging device 82, such as the auxiliary input 84 of MRI scanner 86 illustrated in FIG. 3 and is used to trigger the start of an image data acquisition sequence such as, for example, an fMRI scan. While DBS waveform emulator 32 is depicted as a standalone device in FIG. 1, it is contemplated that the components or the software equivalents thereof can be incorporated directly within computer 74 or imaging device 82 in alternative embodiments.

Figure 3:
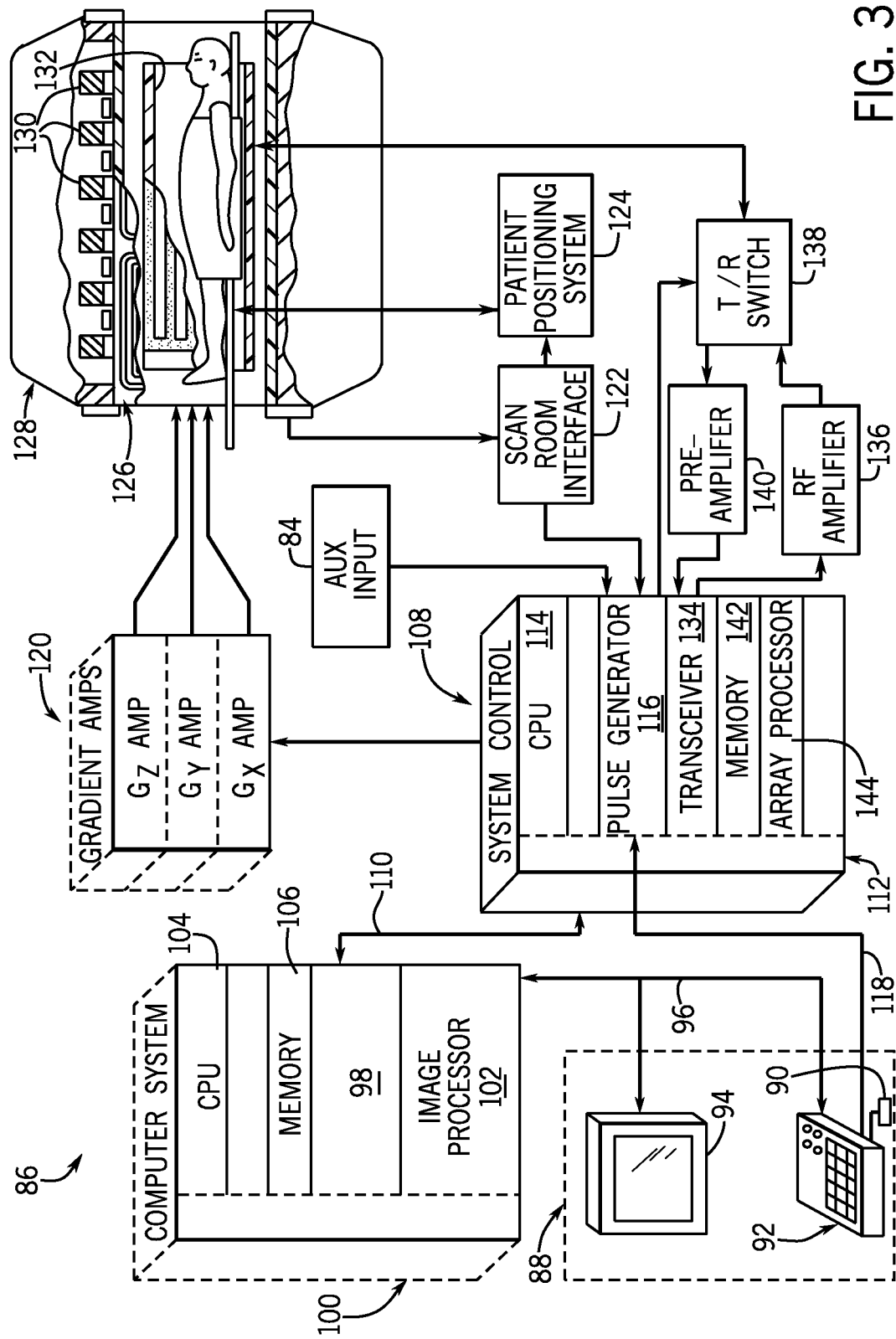
FIG. 3 is a schematic block diagram of an exemplary MR imaging system for use with an embodiment of the invention.

Referring now to FIG. 3, the major components of a MRI scanner 86 useable with the DBS detection system 10 of FIG. 1 are shown according to an exemplary embodiment of the invention. The operation of the MM scanner 86 is controlled for certain functions from an operator console 88, which in this example includes a keyboard or other input device 90, a control panel 92, and a display screen 94. The operator console 88 communicates through a link 96 with a separate computer system 98 that enables an operator to control the production and display of images on the display screen 94. The computer system 98 includes a number of modules which communicate with each other through a backplane 100. These modules include an image processor module 102, a CPU module 104 and a memory module 106, known in the art as a frame buffer for storing image data arrays. The computer system 98 communicates with a separate system control 108 through a high speed serial link 110. The input device 90 can include a mouse, joystick, keyboard, track ball, touch activated screen, light wand, voice control, card reader, push-button, or any similar or equivalent input device, and may be used for interactive geometry prescription.

The system control 108 includes a set of modules connected together by a backplane 112. These include a CPU module 114 and a pulse generator module 116 which connects to the operator console 88 through a serial link 118. It is through serial link 118 that the system control 108 receives commands from the operator to indicate the scan sequence that is to be performed. The pulse generator module 116 operates the system components to carry out the desired scan sequence and produces data which indicates the timing, strength and shape of the RF pulses produced, and the timing and length of the data acquisition window. The pulse generator module 116 connects to a set of gradient amplifiers 120, to indicate the timing and shape of the gradient pulses that are produced during the scan. The pulse generator module 116 can also receive timing data through an auxiliary trigger input 84, which may be coupled to output of the DBS waveform emulator 32 of FIG. 1. And finally, the pulse generator module 116 connects to a scan room interface circuit 122 which receives signals from various sensors associated with the condition of the patient and the magnet system. It is also through the scan room interface circuit 122 that a patient positioning system 124 receives commands to move the patient to the desired position for the scan.

The gradient waveforms produced by the pulse generator module 116 are applied to the gradient amplifier system 120 having Gx, Gy, and Gz amplifiers. Each gradient amplifier excites a corresponding physical gradient coil in a gradient coil assembly generally designated 126 to produce the magnetic field gradients used for spatially encoding acquired signals. The gradient coil assembly 126 forms part of a resonance assembly 128 which includes a polarizing magnet 130 and a whole-body RF coil 132. A transceiver module 134 in the system control 108 produces pulses which are amplified by an RF amplifier 136 and coupled to the whole-body RF coil 132 by a transmit/receive switch 138. The resulting signals emitted by the excited nuclei in the patient may be sensed by the same whole-body RF coil 132 and coupled through the transmit/receive switch 138 to a preamplifier 140. The amplified MR signals are demodulated, filtered, and digitized in the receiver section of the transceiver module 134. The transmit/receive switch 138 is controlled by a signal from the pulse generator module 116 to electrically connect the RF amplifier 136 to the whole-body RF coil 132 during the transmit mode and to connect the preamplifier 140 to the whole-body RF coil 132 during the receive mode. The transmit/receive switch 138 can also enable a separate RF coil (for example, a surface coil) to be used in either the transmit or receive mode.

The MR signals picked up by the whole-body RF coil 132 are digitized by the transceiver module 134 and transferred to a memory module 142 in the system control 108. A scan is complete when an array of raw k-space data has been acquired in the memory module 142. This raw k-space data is rearranged into separate k-space data arrays for each image to be reconstructed, and each of these is input to an array processor 144 which operates to Fourier transform the data into an array of image data. This image data is conveyed through the serial link 110 to the computer system 98 where it is stored in memory. In response to commands received from the operator console 88 or as otherwise directed by the system software, this image data may be archived in long term storage or it may be further processed by the image processor module 102 and conveyed to the operator console 88 and presented on the display screen 94.

Figure 4:
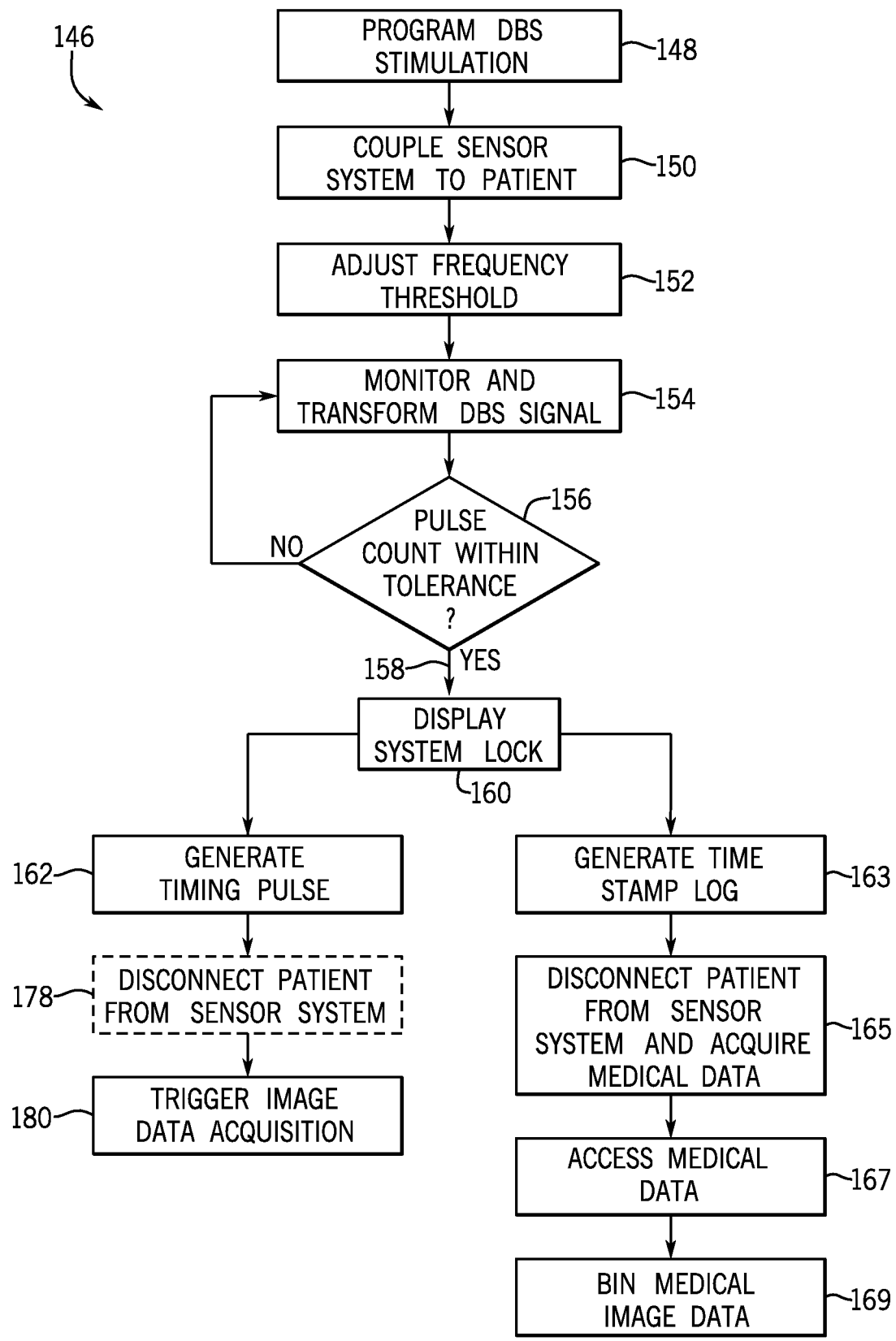
FIG. 4 is a flowchart illustrating a technique for analyzing the DBS stimulation parameters, according to an embodiment of the invention.

Referring to FIG. 4 in conjunction with the elements of FIGS. 1-3 where appropriate, a DBS excitation prediction technique 146 is illustrated according to an embodiment of the invention. Technique 146 begins at step 148 by setting pulse generator 20 to generate a cyclic DBS excitation pattern using programming device 22. This cyclic excitation pattern causes implanted electrodes 12 deliver stimulation pulses during a set "active" or ON period followed by a set "non-active" period wherein the implanted electrodes 12 are OFF. In one embodiment, the duration of the ON and OFF periods may be selected based on the resolution of the type of data acquisition being synchronized with the DBS stimulation. For example, in embodiments where the DBS stimulation is used to trigger fMRI acquisition, the DBS stimulation is programmed to set a cyclic ON/OFF pattern where the duration of each ON and OFF period is multiple seconds, such as 20 seconds ON and 10 seconds OFF as one non-limiting example. In alternative embodiments where the DBS stimulation is synchronized with data acquisition that occurs at millisecond resolution, such as EEG, the duration of each ON and OFF period may be shortened accordingly.

At step 150, sensor system 24 is coupled to or positioned in close proximity of the patient 16 in a manner that permits sensor system 24 to sense bioelectrical signals generated within the patient 16 responsive to a DBS. In one embodiment, bioelectrical sensors 26 are affixed to the patient 16 while the patient 16 remains outside the MRI scanner 86. Alternatively, the bioelectrical sensors 26 may remain affixed to the patient 16 when the patient 16 is introduced to the MRI scanner 86.

At step 152, adjustment dial 48 is manipulated until the reported frequency of the amplified signal received from sensor system 24 corresponds to the frequency DBS signal of the particular patient 16. In embodiments where DBS waveform emulator 32 includes optional dials 56, 58, the operator may also set the total expected, programmed period and the expected frequency programmed in the pulse generator 20 via dials 56, 58 at step 152.

The DBS excitation signal received from sensors 26 is monitored and transformed into a series of digital logic pulses at step 154 after passing through the various circuitry elements of DBS waveform emulator 32. As described in detail with respect to FIG. 2, the series of digital logic pulses represents active or ON portions of the cyclic DBS excitation, with each active or ON portion including numerous individual digital logic pulses corresponding to individual electrode triggers. Technique 146 uses accumulated data to measure the timing of the cyclic ON/OFF excitation pattern generated from the DBS signal and maintains a pulse count for the accumulated data.

The DBS waveform emulator 32 determines whether the pulse count is within a predetermined threshold at step 156. This predetermined threshold is an integer value that may be programmed on microprocessor 54 or selected by an operator prior to an imaging procedure according to alternative embodiments. Once a predetermined number of pulses (within a desired tolerance) are measured 158, microprocessor 54 generates an output signal that causes lock light 64 to illuminate at step 160, indicating that the sensor system 24 may be disconnected from the patient 16.

In embodiments that include period and/or frequency dials 56, 58, the amount of time prior to system lock is reduced through microprocessor 54, which measures and records timing of the ON/OFF portions of the analyzed signals and discards values that fall outside a predefined tolerance of the expected period. Once a preset number of measured pulses are acquired that fall within the predefined tolerance, lock light 64 illuminates.

After system lock, the DBS excitation pattern detected by sensor system 24 may be converted to a timing signal 78 that includes a series of timing pulses at step 162. This series of timing pulses simulates the envelope of the cyclic DBS excitation signal based on the accumulated data and predicts timing of the future DBS excitation signal generated by pulse generator 20. In one embodiment, microprocessor 54 measures the frequency and period corresponding to each ON/OFF pulse, discards outlying data, and generates a timing signal predictive of the DBS excitation pattern from a subset of the accumulated data that fall within predefined tolerances. Each timing pulse of the timing signal has a pulse width that approximates the pulse width of active or ON portions of the cyclic DBS excitation pattern. The pulse width is determined by calculating an average duration of the active portions of the DBS excitation based on the recorded data.

Figure 5:
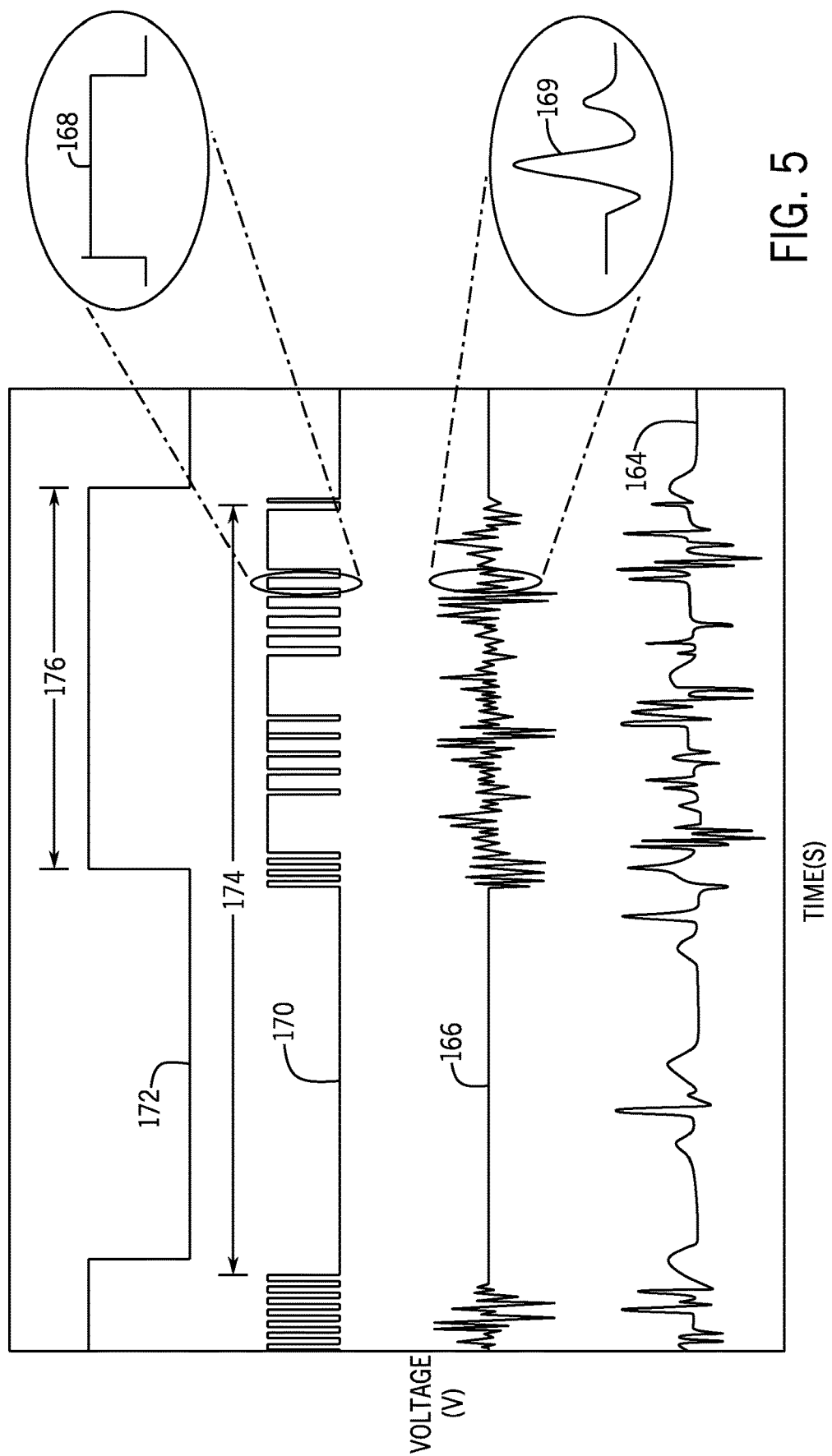
FIG. 5 illustrates raw and filtered waveforms corresponding to an exemplary DBS stimulation.

After DBS waveform emulator 32 is locked on the waveform representing the DBS excitation pattern of the patient 16, DBS waveform emulator 32 may be configured to monitor the time-difference between the predicted and measured DBS stimulation state while the patient 16 remains connected to the sensor system 24. This assessment is carried by comparing the timing of the pulse envelope converted from the real-time signal output from sensor system 24 to the predicted timing of the pulse envelope as determined based on the average of the data received from the sensor system 24 prior to system lock. The calculated time-difference between the predicted and measured DBS state (i.e., wander) may be displayed on LCD display 70. Further, this wander or time offset may be calculated at various points during an MRI examination by reconnecting the patient 16 to the sensor system 24 in order to access the accuracy of the synchronization of the image acquisition timing. At any point during or after the signal conversion, the output signal or waveform corresponding to each of these steps may be displayed to an operator such as on display 70 (FIG. 1) and/or stored within a database 76. Exemplary waveforms corresponding to the various stages of the DBS signal transformation are illustrated in FIG. 5. It will be understood that these waveforms are provided for explanatory purposes only and would vary based on the particulars of the given DBS stimulation. Trace 164 represents the raw input signal received by DBS waveform emulator 32 during a given DBS. In addition to signals corresponding to the DBS, the raw trace 164 includes heart signals and may include transients at the start of pulse generator 20. The central trace 166 represents the signal after passing through the high pass filter 44, which removes the electrical response from cardiac activity. After passing through DC-blocking capacitor 50, comparator circuit 46, and pulse stretcher 52, the high-pass filtered signal is converted into a series of individual digital logic pulses 168 that replicate the excitation timing 169 of the implanted electrodes 12, as illustrated by trace 170. The final trace 172 represents the output timing signal 78 used to trigger fMRI image acquisition, which replicates the envelope 174 of the cyclic ON/OFF excitation pattern of the DBS and includes a series of timing pulses that have a pulse width 176 that approximates the average duration of an ON portion of the excitation pattern and represents the starting time and stopping time of the ON portion, which are used to synchronize MRI image acquisition.

Referring again to FIG. 4, after locking onto the cyclic stimulation pattern generated by the internal pulse generator 20, the bioelectrical sensors 26 are optionally disconnected from the patient 16 at step 178. The patient 16 enters the MRI scanner 86 free of any components of sensor system 24 and the TTL timing signal predictive of the DBS waveform continues to be output by microprocessor 54 based upon an average of the data acquired from sensor system 24 prior to disconnection. Alternatively, the patient 16 may enter the MRI scanner 86 with the sensor system 24 still connected to the patient 16. In such an embodiment, sensor system 24 is constructed of components that are compatible with the imaging system such that the sensor system 24 may remain affixed to the patient 16 during image acquisition. According to one embodiment, microprocessor 54 continues to receive and process data from sensor system 24 after the patient 16 enters the MM scanner 86 until just prior to image acquisition, at which point the sensor system 24 is turned off. Alternatively, sensor system 24 may be configured to continue to acquire data during image acquisition. In such embodiments, DBS waveform emulator 32 may be configured with an additional filter (not shown) designed to filter out imaging gradients in the signals received from sensor system 24.

At step 180 fMRI acquisition is configured with a periodicity equal to the DBS periodicity measured by DBS waveform emulator 32. Once the fMRI sequence is armed, the first trigger provided by the DBS waveform emulator 32 indicating the predicted start of an ON portion of the DS excitation will trigger the fMRI scan. The acquired image data is synchronized with the DBS excitation pattern, allowing data acquired during the stimulus (ON period) to be compared with data acquired during the OFF period to assess the neurological impact of the DBS.

After identifying a system lock at step 160, technique 146 may alternatively generate a time stamp log at step 163, which may be later used to bin medical images acquired during a DBS. In such an embodiment, the DBS waveform emulator 32 records the timing of the ON and OFF periods of the DBS based on a reference time output by the clock 55 provided within the DBS waveform emulator 32. The series of digital logic pulses is then used to predict the future timing pattern of the excitation signal. A time stamp log is generated from the predicted future timing pattern and is synchronized with the reference time output of the clock 55. The predicted future timing pattern is determined in a similar manner as the timing pulses described with respect to step 162 based on calculated average durations of the active (ON) periods of the DBS excitation as determined from the acquired DBS signal. Each time stamp of the time stamp log reflects the predicted start time of future active transmission periods or ON periods of the cyclic DBS excitation. The time stamp log may additionally include predicted start times of the future non-active (OFF) periods and/or information regarding the predicted pulse width or envelope of the ON periods.

The patient is disconnected from the sensor system at step 165 and medical data is acquired from the patient thereafter. The medical data is acquired during the cyclic DBS excitation and is time stamped for later analysis. According to various embodiments, the medical data may include image data that is later reconstructed into MRI images, fMRI images, PET images, or optical images, or data acquired from non-imaging modalities such as, for example, EEG or MEG. However, one skilled in the art will recognize that the techniques described herein may be extended for use any type of medical data that might yield data reflective of the anatomical or functional response of a DBS system. The time-stamped medical data (or the images reconstructed therefrom) is later accessed at step 167 and correlated with the DBS time stamp log at step 169. During this binning step, the DBS time stamp log is used to identify the medical data or images acquired during active periods and non-active periods of neurological excitation based on a correlation with the time stamps of the medical data.

Accordingly, embodiments of the present invention beneficially provide an apparatus and method that is independent from the DBS programmer and that identifies the excitation pattern of the DBS signal based on bioelectrical signals produced within the patient during a DBS excitation. The disclosed apparatus and method process the detected bioelectrical signals into a series of digital logic pulses that are used to emulate the DBS waveform. According to various embodiments, this emulated DBS waveform may be used to predict the future timing sequence of the DBS excitation after the sensor system is disconnected from the patient or in the presence of interference generated by an imaging device such as an MRI scanner. The predicted timing sequence of the DBS excitation may then be used to directly trigger image data acquisition synchronized to ON or active periods of the DBS excitation or be used to generate a time stamp log that may be used to correlate medical data to ON and OFF periods of the DBS excitation. The emulated DBS waveform may further be used to assess the health of the DBS system, by permitting an operator to determine whether the timing sequence of the DBS excitation is being carried out in accordance with the DBS programming.

A technical contribution for the disclosed method and apparatus is that it provides for a computer implemented system and method for detecting the excitation pattern of a DBS and converting the detected excitation pattern into a timing pulse that permits image data acquisition to be synchronized with the DBS. The disclosed method and apparatus further provides for a computer implemented system and method for predicting a future timing pattern of a DBS excitation signal and generating a time stamp log predictive of future active transmission periods of neurological excitation therefrom.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Therefore, according to one embodiment of the invention, an apparatus for analyzing bioelectrical signals generated during a deep brain stimulation (DBS) includes a housing having a signal input and a signal output and an electrical circuit disposed within the housing and electrically coupled between the signal input and the signal output. The electrical circuit is configured to receive bioelectrical signals corresponding to a cyclic excitation signal transmitted by a pulse generator during a DBS and generate an output signal comprising a series of timing pulses, wherein each timing pulse simulates an envelope of the cyclic excitation signal.

According to another embodiment of the invention, a method for analyzing bioelectrical signals generated during a deep brain stimulation (DBS) includes obtaining bioelectrical signals generated from excitation signals transmitted by a pulse generator during a DBS. The method also includes transforming the bioelectrical signals into a series of digital logic pulses representing a plurality of active portions of the DBS, each active portion comprising a plurality of digital logic pulses. The method further includes generating a series of timing pulses from the series of digital logic pulses, each timing pulse synchronized with predicted timing of an active portion of the DBS.

According to yet another embodiment of the invention, a medical imaging system includes an imaging device configured to acquire medical image data from a patient and reconstruct medical images therefrom. The medical imaging system also includes a sensor system configured to detect bioelectrical signals generated within the patient during a deep brain stimulation (DBS) and a DBS signal emulator removeably coupleable to a trigger input of the imaging device and to the sensor system. The DBS signal emulator is programmed to transform bioelectrical signals received from the sensor system into a series of timing pulses having pulse widths predictive of active periods of the DBS and output the series of timing pulses to the trigger input of the imaging device.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An apparatus for analyzing bioelectrical signals generated during a deep brain stimulation (DBS), the apparatus comprising:
    a housing having a signal input and a signal output; and
    an electrical circuit disposed within the housing and electrically coupled between the signal input and the signal output, the electrical circuit configured to:
        receive bioelectrical signals corresponding to a cyclic excitation signal transmitted by a pulse generator during the DBS; and
        generate an output signal comprising a series of timing pulses, wherein each timing pulse in the series of timing pulses simulates an envelope of the cyclic excitation signal.

2. The apparatus of claim 1 wherein the electrical circuit is further configured to:
    transform the bioelectrical signals into a series of digital logic pulses representing a plurality of active portions of the cyclic excitation signal, each active portion in the plurality of active portions comprising a plurality of digital logic pulses in the series of digital logic pulses; and
    wherein the electrical circuit further comprises a processor programmed to define each timing pulse in the series of timing pulses having a pulse width that approximates a duration of an active portion in the plurality of active portions of the DBS.

3. The apparatus of claim 2 wherein the processor is further programmed to:
    record timing of the series of digital logic pulses in real time;
    calculate an average duration of the plurality of active portions of the DBS based on the recorded timing; and
    define the pulse width of the timing pulse based on the calculated average duration.

4. The apparatus of claim 3 wherein the processor is further programmed to:
    count a number of recorded digital logic pulses;
    identify a signal lock if the number of recorded digital logic pulses is within a predetermined threshold; and
    generate the output signal after identifying the signal lock.

5. The apparatus of claim 3 wherein the processor is further programmed to:
    compare timing of the series of digital logic pulses to the series of timing pulses of the generated output signal; and
    calculate a timing offset based on the comparison, the timing offset representing a difference between actual and predicted timing of the cyclic excitation signal.

6. The apparatus of claim 1 wherein the electrical circuit is configured to transform the bioelectrical signals into a series of transistor-transistor logic (TTL) pulses before generating the output signal comprising the series of timing pulses.

7. The apparatus of claim 1 wherein the electrical circuit comprises:
    a comparator circuit that converts the bioelectrical signals into TTL pulses; and
    a pulse stretcher that correlates each TTL pulse that was converted from a bioelectrical signal with a corresponding excitation signal generated during the DBS before generating the output signal comprising the series of timing pulses.

8. The apparatus of claim 1 wherein the signal output of the housing is electrically coupleable to an auxiliary trigger input of an MM system.

9. The apparatus of claim 1 further comprising at least one sensor coupled to the signal input of the housing and coupleable to a patient to receive the bioelectrical signals therefrom during the DBS.

10. The apparatus of claim 1 further comprising an adjustment device positioned on an external surface of the housing and coupled to the electrical circuit, the adjustment device configured to modify a frequency threshold of the received bioelectrical signals.

11. A method for analyzing bioelectrical signals generated during a deep brain stimulation (DBS), the method comprising:
    transmitting excitation signals via a pulse generator;
    obtaining bioelectrical signals derived from the excitation signals transmitted by the pulse generator during the DBS;
    transforming the bioelectrical signals that were derived from the excitation signals into a series of digital logic pulses representing a plurality of active portions of the DBS, each active portion comprising a plurality of digital logic pulses in the series of digital logic pulses;
    predicting a future timing pattern of the excitation signals from the series of digital logic pulses; and
    generating a series of timing pulses from the series of digital logic pulses, wherein each timing pulse in the series of timing pulses is synchronized with the predicted future timing pattern of an active portion of the DBS.

12. The method of claim 11 further comprising generating the series of timing pulses such that each timing pulse in the series of timing pulses represents the plurality of digital logic pulses corresponding to a respective active portion of the DBS.

13. The method of claim 11 further comprising:
    recording timing of the series of digital logic pulses in real time;
    calculating an average duration of the plurality of active portions of the DBS based on the recorded timing; and
    defining a pulse width of the series of timing pulses based on the calculated average duration.

14. The method of claim 11 further comprising:
    outputting the series of timing pulses to a medical imaging device; and
    triggering image data acquisition with the series of timing pulses.

15. The method of claim 11 further comprising:
    transforming the bioelectrical signals into a series of transistor-transistor (TTL) pulses before generating an output signal comprising the series of timing pulses; and
    triggering fMRI image acquisition with the TTL pulses.

16. The method of claim 11 further comprising generating the series of timing pulses such that each timing pulse has a pulse width corresponding to a duration of an active portion of the plurality of active portions of the DBS.

17. A medical imaging system comprising:

an imaging device configured to acquire medical image data from a patient and reconstruct medical images therefrom;

a sensor system configured to detect bioelectrical signals generated within the patient during a deep brain stimulation (DBS); and a DBS signal emulator removeably coupleable to the imaging device and to the sensor system, the DBS signal emulator programmed to:

transform the bioelectrical signals received from the sensor system into a series of timing pulses having pulse widths predictive of active periods of the DBS; and output the series of timing pulses to the imaging device.

18. The medical imaging system of claim 17 wherein the DBS signal emulator comprises an electrical circuit disposed within a housing; and wherein the electrical circuit comprises:

circuitry configured to transform the bioelectrical signals into a series of digital logic pulses; and a processor programmed to generate the series of timing pulses from the series of digital logic pulses, each timing pulse in the series of timing pulses having a pulse width that simulates an envelope of a cyclic DBS excitation.

19. The medical imaging system of claim 18 wherein the processor is further programmed to:

record timing of the series of digital logic pulses in real time;

count the recorded series of digital logic pulses; and output a signal lock indicator if the count exceeds a predefined threshold.

20. The medical imaging system of claim 17 wherein the imaging device comprises a magnetic resonance imaging (MRI) device; and wherein the series of timing pulses trigger MRI image acquisition.

* * * * *